US010159502B2

(12) United States Patent
Wu et al.

(10) Patent No.: US 10,159,502 B2
(45) Date of Patent: Dec. 25, 2018

(54) ARTHROSCOPIC POSITIONING INSTRUMENT

(71) Applicant: E-DA HEALTHCARE GROUP, Kaohsiung (TW)

(72) Inventors: Chin-Hsien Wu, Kaohsiung (TW); Ting-Sheng Lin, Kaohsiung (TW); Jiun-Ru Jiang, Kaohsiung (TW)

(73) Assignee: E-DA HEALTHCARE GROUP, Kaohsiung (TW)

( * ) Notice: Subject to any disclaimer, the term of this patent is extended or adjusted under 35 U.S.C. 154(b) by 35 days.

(21) Appl. No.: 15/336,400

(22) Filed: Oct. 27, 2016

(65) Prior Publication Data
US 2018/0064452 A1    Mar. 8, 2018

(30) Foreign Application Priority Data

Sep. 5, 2016 (TW) .............................. 105128652 A

(51) Int. Cl.
*A61B 17/17* (2006.01)
*A61B 17/00* (2006.01)
(52) U.S. Cl.
CPC ...... *A61B 17/17* (2013.01); *A61B 2017/0042* (2013.01); *A61B 2017/00424* (2013.01)
(58) Field of Classification Search
CPC ............ A61B 17/1764; A61B 17/1714; A61B 17/1716; A61B 17/1703–17/1796;
(Continued)

(56) References Cited

U.S. PATENT DOCUMENTS 2,175,632 A * 10/1939 Maga ..................... E05B 1/0015
15/145
5,324,295 A * 6/1994 Shapiro .............. A61B 17/1714
606/86 R
(Continued)

FOREIGN PATENT DOCUMENTS

CN       105455877       4/2016
JP       201224177       2/2012

OTHER PUBLICATIONS

English abstract translation of CN105455877.
US2016/0089161 corresponds to CN105455877.
English abstract translation of JP201224177.

*Primary Examiner* — Zade Coley
*Assistant Examiner* — Jessica Weiss
(74) *Attorney, Agent, or Firm* — WPAT, PC

(57) ABSTRACT

An arthroscopic positioning instrument is provided to overcome the problem of inconvenient operation of the modern arthroscopic positioning instrument. The arthroscopic positioning instrument includes a handle, a positioning member and a guiding cylinder is disclosed. The handle includes a finger holding member, a palm holding member and at least one connecting member. The palm holding member is connected to the finger holding member via the at least one connecting member. The finger holding member includes one end provided with an engaging portion and an arched guiding groove. The palm holding member does not intrude into a maximum axial range of the engaging portion. The positioning member includes an arched end and a hook end. The arched end is received in the arched guiding groove. The guiding cylinder is coupled with the engaging portion of the finger holding member.

18 Claims, 7 Drawing Sheets

(58) Field of Classification Search
CPC .. A61B 2017/00424–2017/00455; B25G 1/00; B25G 1/01; B25G 1/10; B25G 1/102; B25G 1/105
USPC .............. 606/96–98, 104; 81/489; 16/110.1, 16/422–429, 430; 600/197, 213, 226, 234
See application file for complete search history.

(56) References Cited

U.S. PATENT DOCUMENTS

| | | | |
|---|---|---|---|
| 6,120,511 A * | 9/2000 | Chan | A61B 17/1637 606/102 |
| 6,254,605 B1 * | 7/2001 | Howell | A61B 17/1714 606/86 R |
| 2013/0133158 A1 * | 5/2013 | Tran | A47B 95/02 16/422 |
| 2014/0194888 A1 * | 7/2014 | Smith | A61B 17/1714 606/96 |
| 2016/0089161 A1 | 3/2016 | Ardito et al. | |

* cited by examiner

ARTHROSCOPIC POSITIONING INSTRUMENT

CROSS REFERENCE TO RELATED APPLICATIONS

The application claims the benefit of Taiwan application serial No. 105128652, filed on Sep. 5, 2016, and the subject matter of which is incorporated herein by reference.

BACKGROUND OF THE INVENTION

1. Field of the Invention

The present disclosure generally relates to a minimally invasive surgical instrument and, more particularly, to an arthroscopic positioning instrument that can provide a positioning effect to assist the doctor in accurately drilling the holes on a bone of the patient.

2. Description of the Related Art

FIG. 1 shows a conventional surgical positioning instrument 9 including an arched guiding member 91, a drill guiding member 92 and a hook 93. The drill guiding member 92 is coupled with one end of the guiding member 91, and the hook 93 is slidably mounted between two ends of the guiding member 91. An embodiment of such a surgical positioning instrument 9 can be seen in Japanese Patent Publication No. 2012-24177.

When the surgical positioning instrument 9 is in use, a predetermined part of the joint of the patient can be hooked by the hook 93. Then, a drill D can be inserted into the drill guiding member 92. The drill D starts to drill toward the tip of the hook 93 to create a suture path on the bone and cartilage of the patient. The drilling operation is performed twice to create two suture paths. Next, a suture is threaded into one of the suture paths and through the surface of the cartilage, and then threaded out of the cartilage from the other suture path. Thus, the cartilage can be pulled back to the anatomical position by the suture.

However, different joints require different sizes of the surgical positioning instrument 9. If the conventional surgical positioning instrument 9 has a large size (used for a knee joint, for example), the operator can stably hold the guiding member 91 or the drill guiding member 92 to perform the drilling operation. Thus, the drilling operation is smooth and the error is small. However, if the conventional surgical positioning instrument 9 has a small size (used for a wrist joint, for example), the part of the positioning instrument 9 that can be held by the operator is only a few centimeters long which is too small to properly hold. As such, the operator can only hold that part with the fingers rather than with the hand. As another disadvantage, the operator's hand tends to cut off the view of the hole that is being drilled, and the operator needs to carefully drill the suture paths in a very small area to prevent the two suture paths from intersecting with each other. Thus, the drilling operation of the small-size surgical positioning instrument 9 is difficult, and even a slight shaking can cause an improper drilling operation. Due to this, in clinical cases the drilling operation often needs to be repeated due to failure. As a disadvantage, the surgery time is prolonged.

SUMMARY OF THE INVENTION

It is therefore the objective of this disclosure to provide an arthroscopic positioning instrument that includes a handle that is easy to grip and dos not cut off the view of the hole that is being drilled.

In an embodiment of the disclosure, an arthroscopic positioning instrument including a handle, a positioning member and a guiding cylinder is disclosed. The handle includes a finger holding member, a palm holding member and at least one connecting member. The palm holding member is connected to the finger holding member via the at least one connecting member. The finger holding member includes one end portion provided with an engaging portion and an arched guiding groove. The palm holding member does not intrude into a maximum axial range of the engaging portion. The positioning member includes an arched end and a hook end. The arched end is received in the arched guiding groove. The guiding cylinder is coupled with the engaging portion of the finger holding member.

Based on this, the arthroscopic positioning instrument of the embodiment of the disclosure includes a handle which permits the operator to hold it in a stable manner. In addition, when the operator holds the handle, the hand of the operator will not prevent viewing of the holes that are being drilled. As such, convenient drilling operation of the suture paths can be attained. Even though in a situation where two suture paths have to be drilled on a small area, the arthroscopic positioning instrument still permits the operator to complete it in an easy way. Thus, it is convenient to operate the arthroscopic positioning instrument, improving the efficiency of the operation and increasing the rate of successful surgery.

In a form shown, the arched guiding groove extends to another end portion of the finger holding member, so that the arched end of the positioning member is able to extend into the arched guiding groove via the other end portion of the finger holding member. As such, convenient assembly and adjustment of the location of the positioning member is attained.

In the form shown, both the finger holding member and the palm holding member are in an arched form. The finger holding member includes an outwardly arched face facing an inwardly arched face of the palm holding member. As such, comfortable holding feeling of the arthroscopic positioning instrument is provided.

In the form shown, the finger holding member includes a through-hole extending from an outer face of the finger holding member to the arched guiding groove, and the finger holding member includes a coupling member extending through the through-hole to abut with the arched end of the positioning member. As such, fast positioning effect of the positioning member can be provided.

In the form shown, the arched guiding groove is formed on one face of the finger holding member, and includes a limiting member aligned with the through-hole and mounted across the arched guiding groove. The coupling member extends through the through-hole to push the arched end of the positioning member against the limiting member. As such, stable positioning effect of the positioning member can be provided.

In the form shown, a side of the arched end of the positioning member that is exposed from the arched guiding groove is provided with graduations. As such, the sliding length of the positioning member can be controlled accurately.

In the form shown, each of the at least one plurality of connecting member comprises two ends respectively connected to two opposing faces of the finger holding member and the palm holding member. As such, convenient operation is attained.

In the form shown, each of the at least one of connecting member includes an outer tube and an inner tube. The outer tube is connected to one of the finger holding member and the palm holding member, and the inner tube is connected to another of the finger holding member and the palm holding member. The inner tube extends into the outer tube by a length, and the length is adjustable. After the length of the inner tube extending into the outer tube is properly adjusted, the inner tube can be fixed in place. As such, comfortable feeling and high stability in operating the arthroscopic positioning instrument can be attained.

In the form shown, each of the outer tube and the inner tube includes a plurality of positioning holes. The inner tube is inserted into the outer tube. One of the plurality of positioning holes of the inner tube is aligned with one of the plurality of positioning holes of the outer tube, and a pin is inserted through the aligned positioning holes of the outer tube and the inner tube to provide a positioning effect. As such, convenient manufacture and operation of the arthroscopic positioning instrument can be attained.

In the form shown, the guiding cylinder includes a head end and a tail end. Each of the head end and the tail end is provided with a cover. The cover includes first and second guiding holes. The first guiding hole of the cover of the head end is coaxial with the first guiding hole of the cover of the tail end, and the second guiding hole of the cover of the head end is coaxial with the second guiding hole of the cover of the tail end. As such, it can be ensured that the suture paths will not intersect from each other.

In the form shown, the first guiding hole has a central axis parallel to a central axis of the second guiding hole. As such, it can be ensured that the suture paths will not intersect from each other.

BRIEF DESCRIPTION OF THE DRAWINGS

The present disclosure will become more fully understood from the detailed description given hereinafter and the accompanying drawings which are given by way of illustration only, and thus are not limitative of the present disclosure, and wherein.

Figure 1:
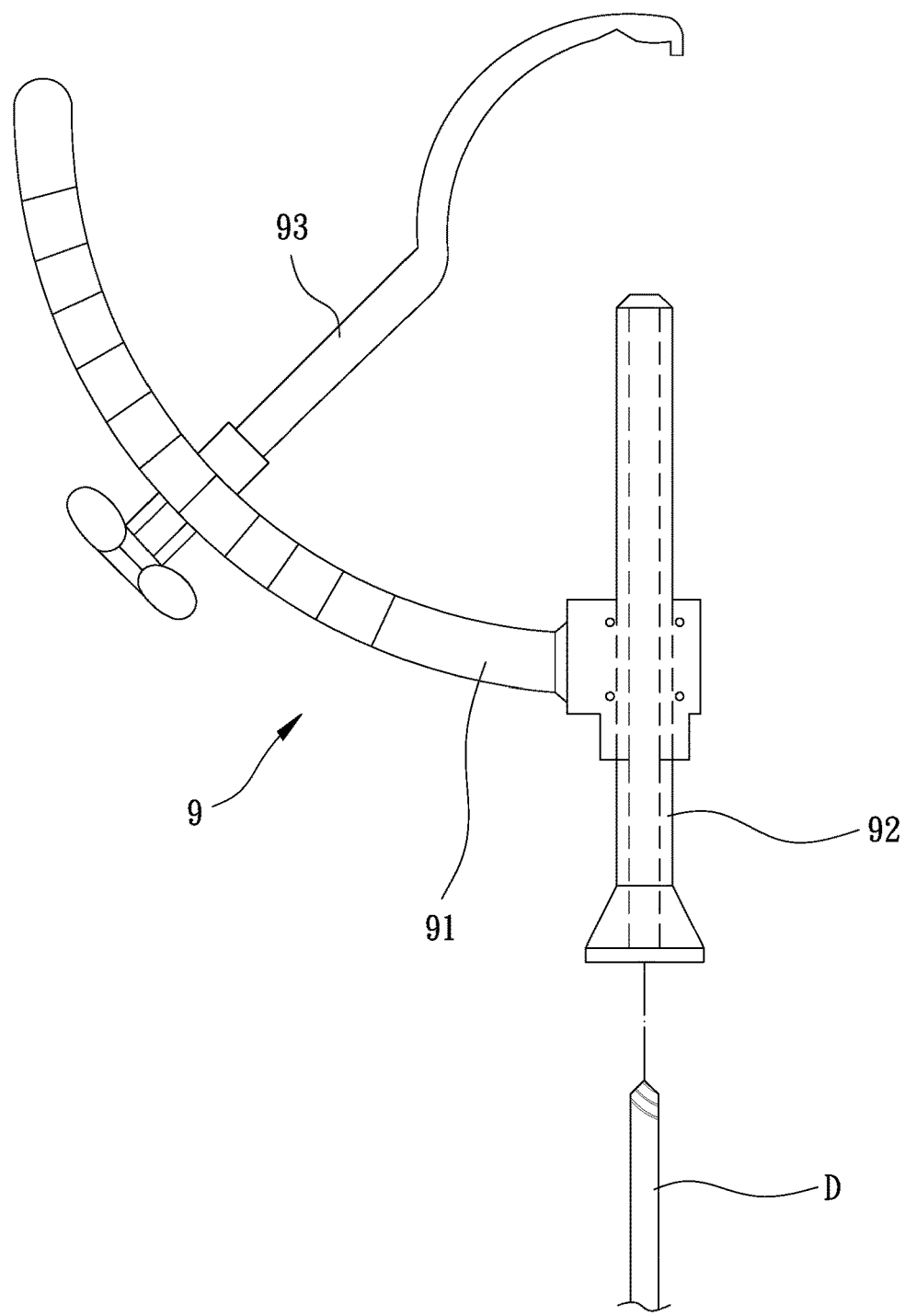
FIG. 1 shows a conventional surgical positioning instrument.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the disclosure.

DETAILED DESCRIPTION OF THE INVENTION

Figure 2:
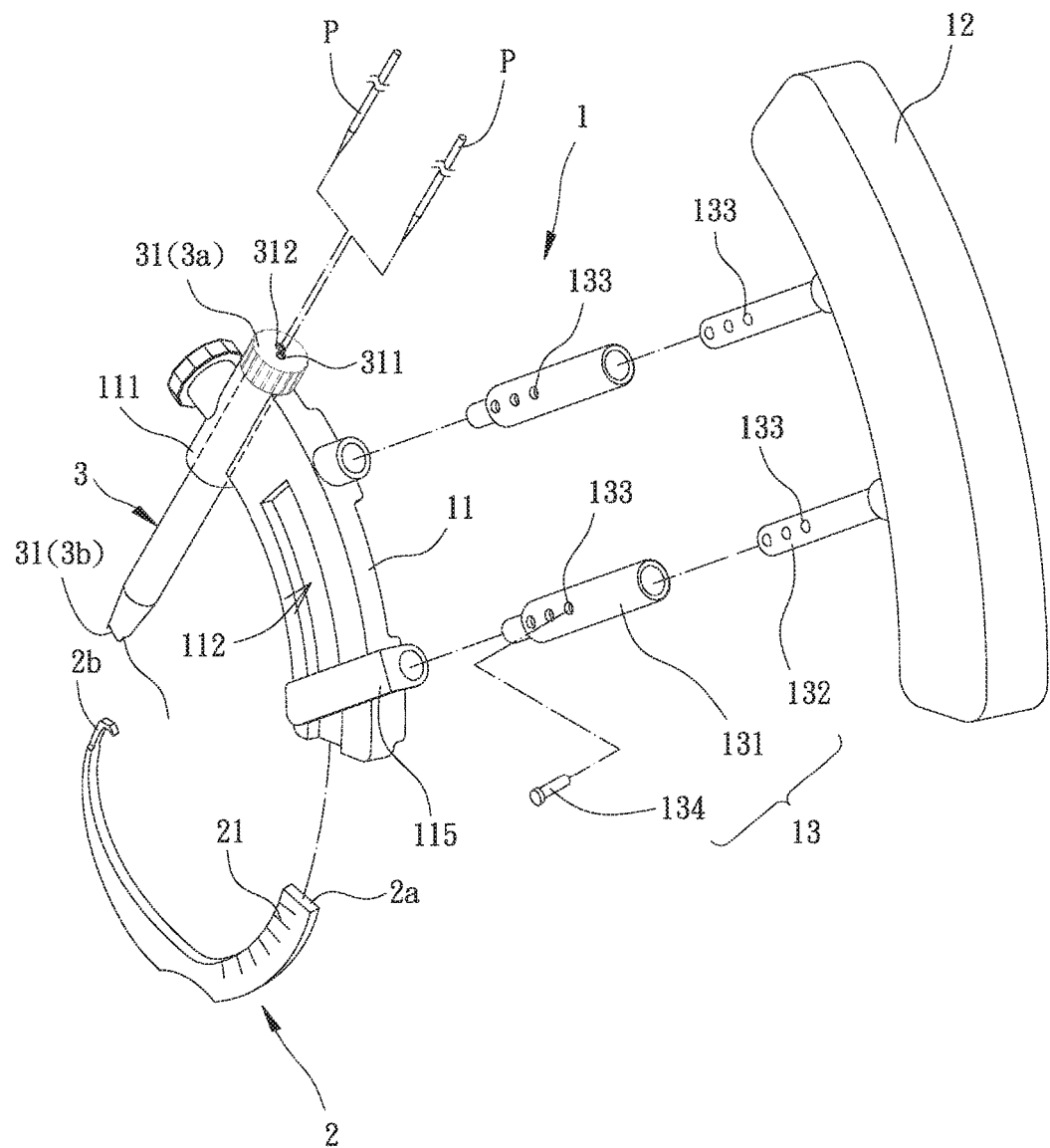
FIG. 2 shows an exploded view of an arthroscopic positioning instrument according to an embodiment of the disclosure.
Figure 3:
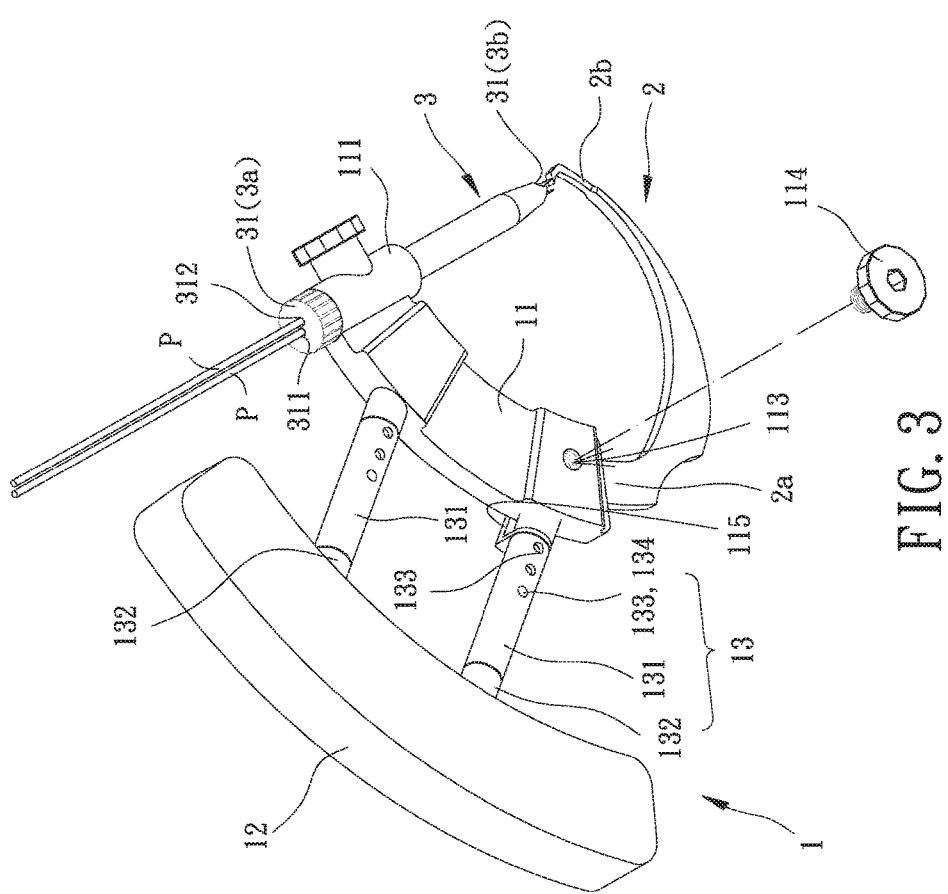
FIG. 3 is another angle of view of the arthroscopic positioning instrument of the embodiment of the disclosure in which the coupling member is not attached to the arthroscopic positioning instrument.

FIGS. 2 and 3 show an exploded view of an arthroscopic positioning instrument according to an embodiment of the disclosure. The arthroscopic positioning instrument includes a handle 1, a positioning member 2 and a guiding cylinder 3. The handle 1 and the positioning member 2 are coupled with two ends of the handle 1, respectively.

The handle 1 includes a finger holding member 11, a palm holding member 12 and at least one connecting member 13. The palm holding member 12 is connected to the finger holding member 11 via the connecting member(s) 13. When the operator holds the handle 1, the thumb and palm can place on the palm holding member 12. The rest of the fingers can place on the finger holding member 11. As such, the operator can hold the handle 1 in a stable manner. To provide a comfortable holding feeling, both the finger holding member 11 and the palm holding member 12 can be designed in an arched form. The outwardly arched face of the finger holding member 11 faces the inwardly arched face of the palm holding member 12.

The finger holding member 11 includes one end portion provided with an engaging portion 111. The engaging portion 111 can be engaged by the guiding cylinder 3. The finger holding member 11 further includes an arched guiding groove 112 that is used to adjust the position of the finger holding member 11. The arched guiding groove 112 has a constant radian so that the ends of the positioning member 2 can map to the same point.

Figure 4:
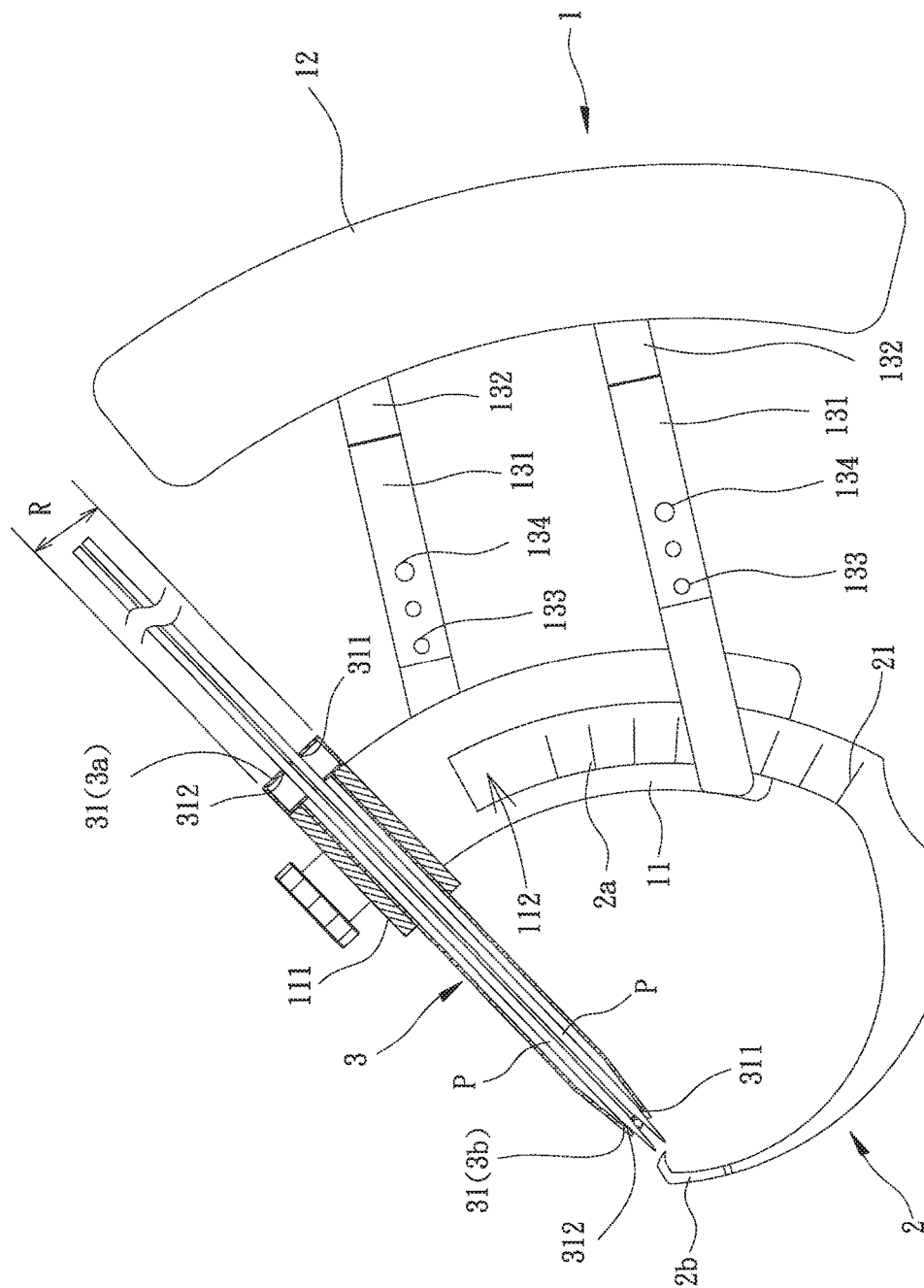
FIG. 4 is a cross sectional view of the arthroscopic positioning instrument of the embodiment of the disclosure.

In the embodiment, the engaging portion 111 can be in the form of a sleeve tube. Therefore, the guiding cylinder 3 can be easily received in the engaging portion 111. The engaging portion 111 has a central axis which may extend through said point of the positioning member 2 (as shown in FIG. 4). The palm holding member 12 does not intrude into a maximum axial range R of the engaging portion 111 in order to prevent the hand of the operator from cutting off the view of the connecting member 13 when the operator holds the handle 1. Optionally, the arched guiding groove 112 can extend to the other end portion of the finger holding member 11, such that the positioning member 2 can be inserted into the arched guiding groove 112 from the other end portion of the finger holding member 11. In this arrangement, the assembly of the positioning member 2 is convenient and the location of the positioning member 2 can be easily adjusted.

The finger holding member 11 can include a through-hole 113 extending from the outer face of the finger holding member 11 to the arched guiding groove 112. The finger holding member 11 can further include a coupling member 114. The coupling member 114 extends through the through-hole 113 to abut with the positioning member 2. Thus, a part of the positioning member 2 can be fixed in a predetermined location of the arched guiding groove 112. Furthermore, in the embodiment, the arched guiding groove 112 is formed on one face of the finger holding member 11, and includes a limiting member 115 aligned with the through-hole 113 and mounted across the arched guiding groove 112. As such, the coupling member 114 can extend through the through-hole 113 to push the positioning member 2 against the limiting member 115.

The quantity and shape of the connecting member(s) 13 is not limited. The connecting member(s) 13 can be in any quantity that is sufficient to securely couple the palm holding member 12 and the finger holding member 11 with each other. Each connecting member 13 includes two ends that are respectively connected to two opposing faces of the finger holding member 11 and the palm holding member 12. As such, the operator cannot easily touch the connecting member(s) 13 during the use of the arthroscopic positioning instrument, thereby providing a smooth use of the arthroscopic positioning instrument. Therefore, convenient use of the arthroscopic positioning instrument is attained.

Each connecting member 13 is preferably adjustable to permit the adjustment of the length between the finger holding member 11 and the palm holding member 12 based on the size of the palm of the operator. Thus, comfortable feeling and higher stability in operating the arthroscopic positioning instrument can be provided. In a non-limiting example, each connecting member 13 may include an outer tube 131 and an inner tube 132. The outer tube 131 is connected to one of the finger holding member 11 and the palm holding member 12, and the inner tube 132 is connected to another of the finger holding member 11 and the palm holding member 12. The length of the inner tube 132 extending into the outer tube 131 can be adjusted. Once the length of the inner tube 132 extending into the outer tube 131 is properly adjusted, the inner tube 132 can be fixed in place. In this arrangement, the length between the finger holding member 11 and the palm holding member 12 can be adjusted as desired. In the embodiment, both the outer tube 131 and the inner tube 132 may include a plurality of positioning holes 133. As such, after the inner tube 132 is inserted into the outer tube 131, one positioning hole 133 of the inner tube 132 may be aligned with one positioning hole 133 of the outer tube 131. Then, a pin 134 may extend through the two positioning holes 133 of the outer tube 131 and the inner tube 132 to provide a positioning effect. This structure is easy to manufacture and operate, and its operation is fast.

The positioning member 2 is used to position the drill in a location where the drilling operation is to be performed. In the embodiment, the positioning member 2 forms an arched end 2a and a hook end 2b. The arched end 2a is slidably received in the arched guiding groove 112. The end 2a has a radian substantially equal to the radian of the arched guiding groove 112, so that the arched end 2a can smoothly slide in the arched guiding groove 112. The arched end 2a can have graduations 21 on the side facing away from the arched guiding groove 112, permitting the operator to accurately control the sliding length of the positioning member 2.

Figure 5:
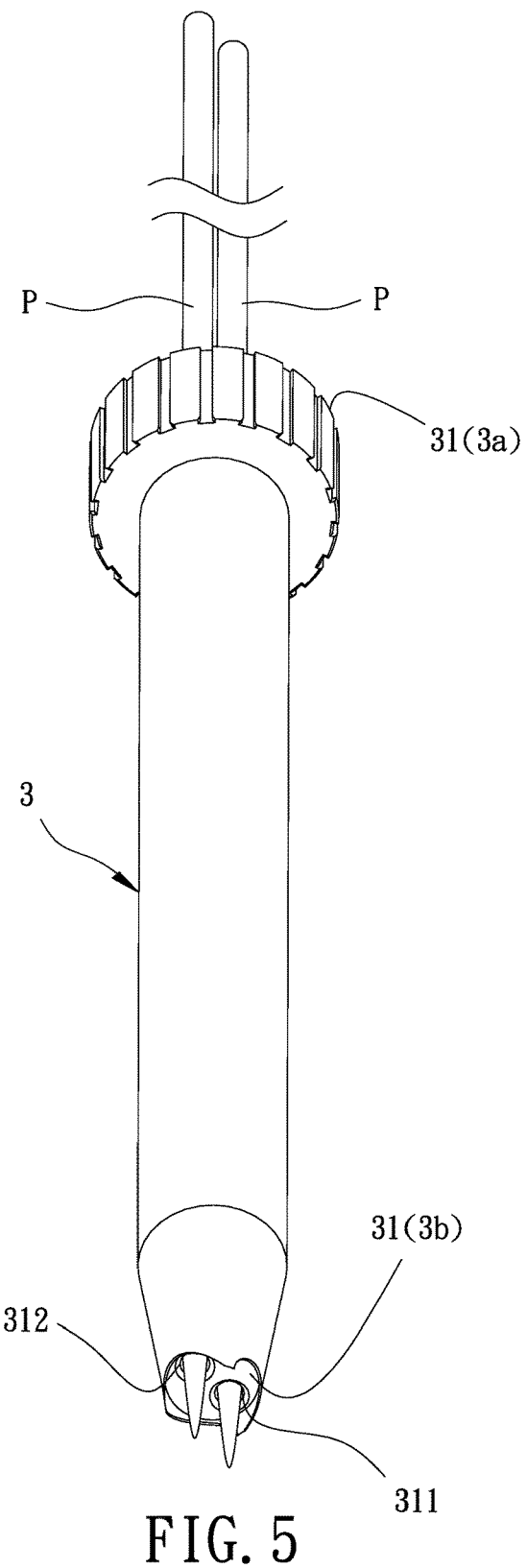
FIG. 5 shows a guiding cylinder of the arthroscopic positioning instrument of the embodiment of the disclosure.

Referring to FIGS. 2, 4 and 5, a plurality of piercing members P can be inserted through the guiding cylinder 3 to the hook end 2b of the positioning member 2. The guiding cylinder 3 is coupled with the engaging portion 111 of the finger holding member 11, and includes a head end 3a and a tail end 3b. Each of the head end 3a and the tail end 3b is provided with a cover 31. The cover 31 includes first and second guiding holes 311 and 312 into which the piercing members P can be inserted. The first guiding holes 311 of the two covers 31 are coaxial with each other, and the second guiding holes 312 of the two covers 31 are coaxial with each other. The central axes of the first and second guiding holes 311 and 312 are preferably parallel to each other, ensuring that the drilled suture paths will not intersect with each other regardless of the length of the suture paths.

Figure 6:
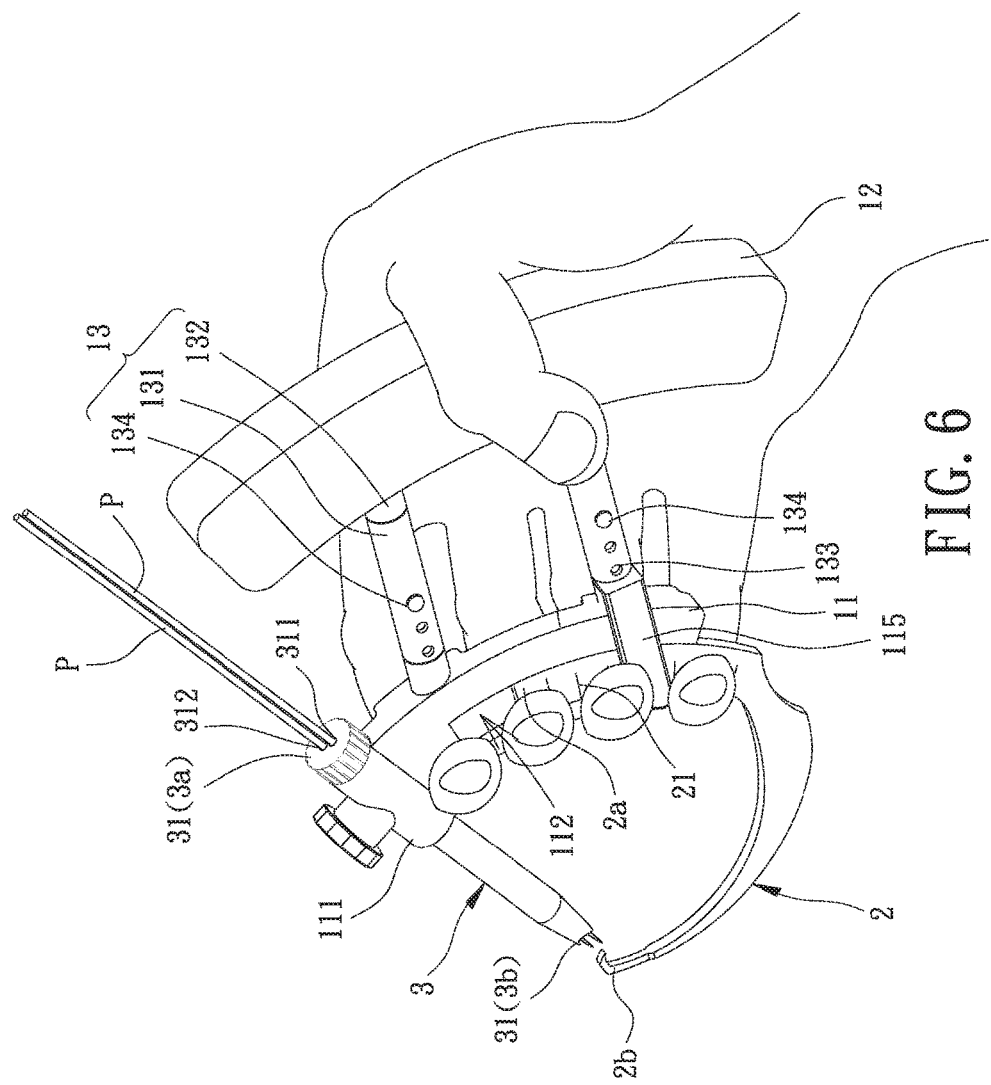
FIG. 6 shows the arthroscopic positioning instrument gripped by a hand of an operator.
Figure 7:
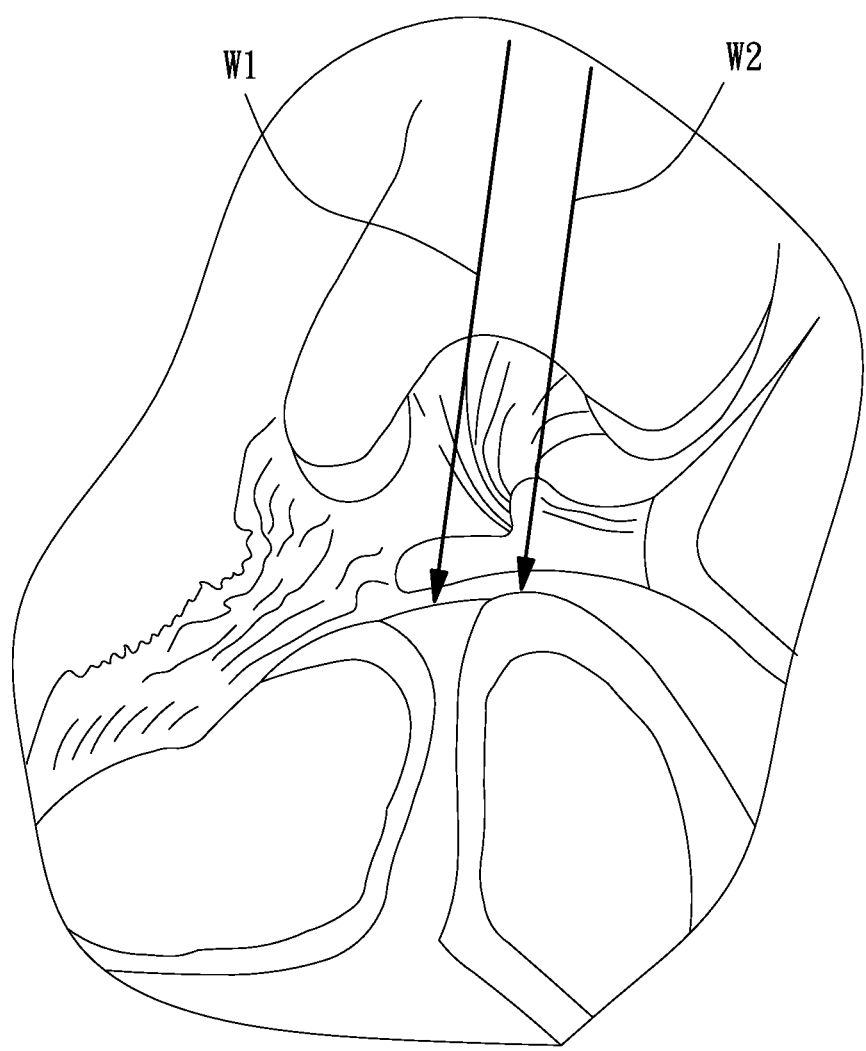
FIG. 7 shows the sutures paths in a suturing procedure of a triangular cartilage.

Based on the above structure, the arthroscopic positioning instrument can be used in a suturing procedure of the triangular cartilage as shown in FIGS. 6 and 7. In this example, the operator can adjust the connecting member(s) 13 according to the size of the palm, so that when the thumb and the palm properly place on the palm holding member 12, the rest of the fingers can fit to the finger holding member 11. As such, the operator can hold the handle 1 in a proper manner. In addition, the position of the arched end 2a of the positioning member 2 in the arched guiding groove 112 is adjusted according to the size of the wrist portion of the patient. During the surgery, the wrist portion of the patient is cut open with a small incision, and the wounded part of the triangular cartilage is hooked by the hook end 2b of the positioning member 2. Next, two piercing members P are inserted into the guiding cylinder 3 to drill two suture paths W1 and W2 on the bone and cartilage of the patient. It should be ensured that the suture paths W1 and W2 can reach the part of the triangular cartilage hooked by the hook end 2b of the positioning member 2 while the two suture paths W1 and W2 do not intersect with each other. Thus, repeated-drilling operation of the suture paths resulting from undesired intersection of the suture paths can be avoided, and the surgery time is not prolonged. Next, a suture is threaded through the suture path W1 and around the surface of the triangular cartilage. Then, a hook wire is threaded into the suture path W2, and one end of the suture is hooked by the hook wire. Based on this, the hook wire and the suture altogether can be pulled out of the body of the patient, so that the triangular cartilage can be pulled back to the anatomical position by the suture.

In summary, the arthroscopic positioning instrument of the embodiment of the disclosure includes a handle which permits the operator to hold it in a stable manner. In addition, when the operator holds the handle, the hand of the operator will not prevent viewing of the holes that are being drilled. As such, convenient drilling operation of the suture paths can be attained. Even though in a situation where two suture paths have to be drilled on a small area, the arthroscopic positioning instrument still permits the operator to complete it in an easy way. Thus, it is very convenient to operate the arthroscopic positioning instrument, improving the efficiency of the operation and increasing the rate of successful surgery.

Although the disclosure has been described in detail with reference to its presently preferable embodiments, it will be understood by one of ordinary skill in the art that various modifications can be made without departing from the spirit and the scope of the disclosure, as set forth in the appended claims.

What is claimed is:

1. An arthroscopic positioning instrument comprising:
a handle having a finger holding member, a palm holding member and at least one connecting member, wherein the palm holding member is connected to the finger holding member via the at least one connecting member, wherein the finger holding member comprises one end portion provided with an engaging portion and an arched guiding groove;
a positioning member having an arched end and a hook end, wherein the arched end is received in the arched guiding groove; and
a guiding cylinder coupled with the engaging portion of the finger holding member,
wherein the finger holding member comprises a through-hole extending from an outer face of the finger holding member to the arched guiding groove, and wherein the finger holding member comprises a coupling member extending through the through-hole to abut with the arched end of the positioning member.

2. The arthroscopic positioning instrument as claimed in claim 1, wherein the arched guiding groove extends to another end portion of the finger holding member, so that the arched end of the positioning member is able to extend into the arched guiding groove via the other end portion of the finger holding member.

3. The arthroscopic positioning instrument as claimed in claim 2, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

4. The arthroscopic positioning instrument as claimed in claim 1, wherein both the finger holding member and the palm holding member are in an arched form, and the finger holding member comprises an outwardly arched face facing an inwardly arched face of the palm holding member.

5. The arthroscopic positioning instrument as claimed in claim 4, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

6. The arthroscopic positioning instrument as claimed in claim 1, wherein the arched guiding groove is formed on one face of the finger holding member, and comprises a limiting member aligned with the through-hole and mounted across the arched guiding groove, wherein the coupling member extends through the through-hole to push the arched end of the positioning member against the limiting member, and wherein the limiting member has a first end mounted to one side of the finger holding member relatively distant to the palm holding member, as well as a second end mounted to another side of the finger holding member relatively adjacent to the palm holding member.

7. The arthroscopic positioning instrument as claimed in claim 6, wherein a side of the arched end of the positioning member that is exposed from the arched guiding groove is provided with graduations.

8. The arthroscopic positioning instrument as claimed in claim 7, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

9. The arthroscopic positioning instrument as claimed in claim 6, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

10. The arthroscopic positioning instrument as claimed in claim 1, wherein each of the at least one connecting member comprises two ends respectively connected to two opposing faces of the finger holding member and the palm holding member.

11. The arthroscopic positioning instrument as claimed in claim 10, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

12. The arthroscopic positioning instrument as claimed in claim 1, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

13. The arthroscopic positioning instrument as claimed in claim 12, wherein the first guiding hole has a central axis parallel to a central axis of the second guiding hole.

14. The arthroscopic positioning instrument as claimed in claim 1, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

15. An arthroscopic positioning instrument comprising:
a handle having a finger holding member, a palm holding member and at least one connecting member, wherein the palm holding member is connected to the finger holding member via the at least one connecting member, wherein the finger holding member comprises one end portion provided with an engaging portion and an arched guiding groove, wherein each of the at least one connecting member comprises two ends respectively connected to two opposing faces of the finger holding member and the palm holding member, wherein each of the at least one connecting member comprises an outer tube and an inner tube, wherein the outer tube is connected to one of the finger holding member and the palm holding member, and the inner tube is connected to another of the finger holding member and the palm holding member, wherein the inner tube extends into the outer tube by a length, and wherein the length is adjustable;
a positioning member having an arched end and a hook end, wherein the arched end is received in the arched guiding groove; and
a guiding cylinder coupled with the engaging portion of the finger holding member.

16. The arthroscopic positioning instrument as claimed in claim 15, wherein each of the outer tube and the inner tube includes a plurality of positioning holes, wherein one of the plurality of positioning holes of the inner tube is aligned with one of the plurality of positioning holes of the outer tube, and wherein a pin is inserted through the aligned positioning holes of the outer tube and the inner tube.

17. The arthroscopic positioning instrument as claimed in claim 16, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

18. The arthroscopic positioning instrument as claimed in claim 15, wherein the guiding cylinder comprises a head end and a tail end, wherein each of the head end and the tail end is provided with a cover, wherein the cover comprises first and second guiding holes, wherein the first guiding hole of the cover of the head end is coaxial with the first guiding hole of the cover of the tail end, and the second guiding hole of the cover of the head end is coaxial with the second guiding hole of the cover of the tail end.

* * * * *